United States Patent [19]

Sheridan et al.

[11] 4,052,887
[45] Oct. 11, 1977

[54] ULTRASONIC TESTING DEVICE AND METHOD

[75] Inventors: Lee A. Sheridan, Lombard; Gary S. Kovener; Bernard Ostrofsky, both of Naperville; Hilbert J. Nebelsiek, Aurora, all of Ill.

[73] Assignee: Standard Oil Company, Chicago, Ill.

[21] Appl. No.: 673,706

[22] Filed: Apr. 5, 1976

[51] Int. Cl.² .......................................... G01N 29/00
[52] U.S. Cl. ................................................ 73/67.8 S
[58] Field of Search ................. 73/67.5 R, 67.6, 67.7, 73/67.8 R, 67.8 S; 308/DIG. 8

[56] References Cited

U.S. PATENT DOCUMENTS

| 3,848,461 | 11/1974 | Hetherington et al. | 73/67.8 S X |
| 3,955,425 | 5/1976 | Corneau | 73/67.8 S X |

Primary Examiner—Jerry W. Myracle
Attorney, Agent, or Firm—Frank J. Sroka; Arthur G. Gilkes; William T. McClain

[57] ABSTRACT

This invention relates to an apparatus and method for non-destructive ultrasonic testing, such as flaw detection and thickness measurement, of elongated bodies, such as pipes and rods or coatings thereon. Ultrasonic signals are sent and received by transducers held in a rotating member while being substantially submersed in an acoustically transmitting liquid such as water. The rotating member is supported by bearings which are resistant to the transmitting liquid.

20 Claims, 3 Drawing Figures

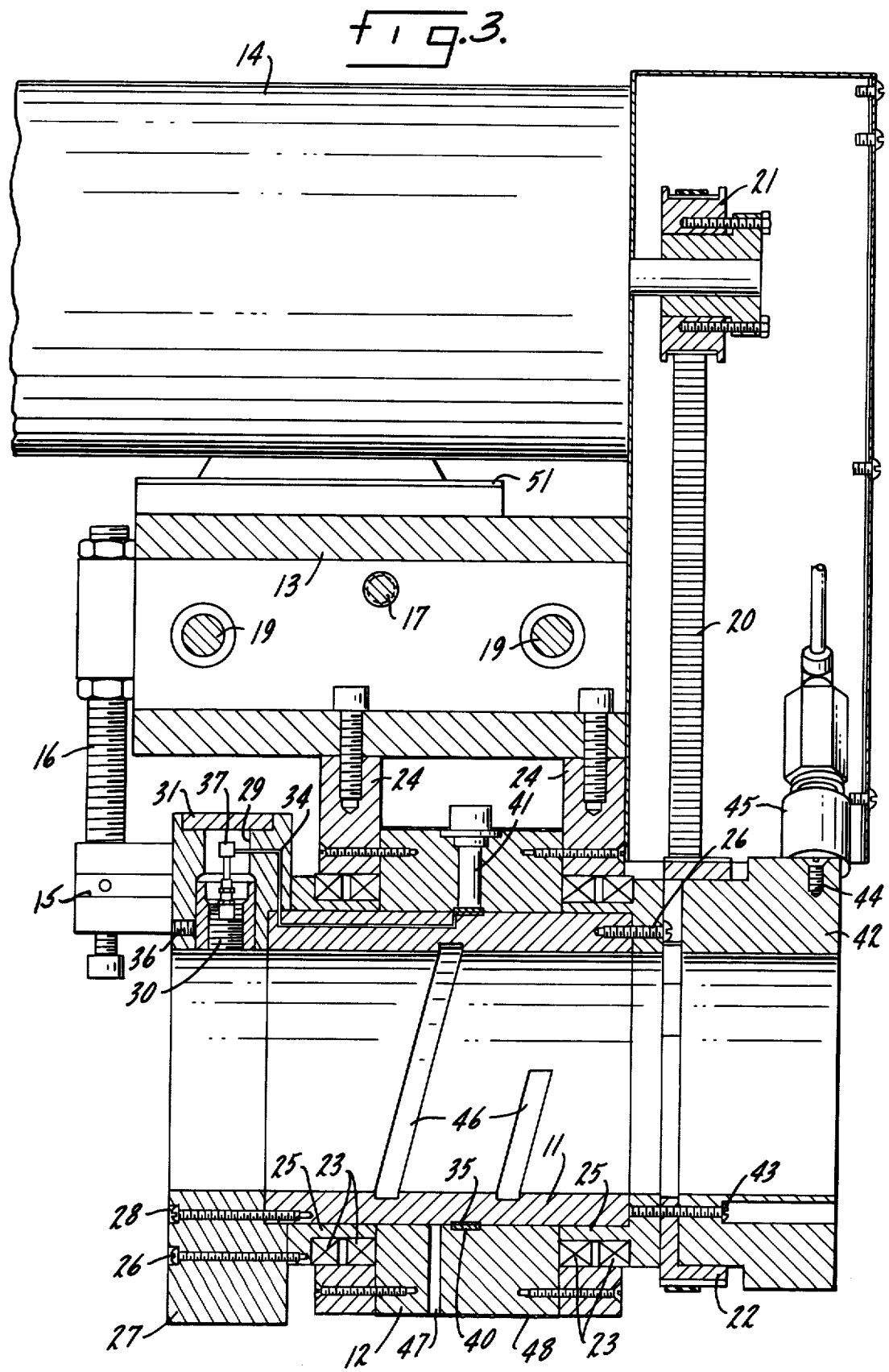

ULTRASONIC TESTING DEVICE AND METHOD

BACKGROUND

This invention relates to an apparatus for non-destructive ultrasonic testing such as detection of flaws or thickness measurement of a material. This invention has particular importance in the testing of elongated materials such as pipes and rods.

Application of a voltage pulse to a piezoelectric crystal will cause it to mechanically oscillate at its resonant frequency. Sound, at the resonant frequency of the crystal will, when it strikes the crystal, also cause oscillation. When the crystal oscillates, it generates a sinusodial voltage and a high frequency sound wave, both of which occur at the crystal's resonant frequency.

In ultrasonic flaw-detector and thickness-measuring instruments, a piezoelectric crystal (transducer) is placed on or near the surface of the body whose integrity or thickness is to be measured. In order to insure effective coupling between the transducer and the surface, the space between may be filled with an acoustically transparent material, i.e., a material having a small amount of accoustical attenuation such as water or oil. The output of a pulse generator, consisting of short duration voltage pulses, is applied to the crystal. In thickness-measuring instruments, high frequency sound generated by the crystal when it is pulsed passes through the body, is reflected from the opposite surface, and returns to the crystal where the back-reflected sound causes the crystal to again oscillate. The same sequence of events may happen repeatedly and there may be a second, third or even greater number of back-reflections due to the same voltage pulse. The voltage pulse initiating this sequence is called the initial pulse. By measuring the elapsed time between the initial pulse and a back-reflection or, between two back-reflections, and knowing the velocity of sound through the body being tested, the thickness can be determined. Similar technique is used in flaw detection.

Ultrasonic pulse-echo thickness-measurement apparatus generally consists of a highly damped piezoelectric transducer excited by an ultrasonic pulse generator connected thereto. Ultrasonic pulses of short duration are injected into a specimen such as a plate metal to determine the thickness D thereof. After entering the specimen, the ultrasonic pulse is repeatedly reflected back and forth between the parallel surfaces of the specimen separated by the dimension D until its energy is dissipated. During this reverberation process, piezoelectric transducer (which also acts as an ultrasonic receiver) generates a short voltage pulse each time the ultrasonic pulse strikes upon the specimen surface to which the piezoelectric transducer is coupled. Thus, following the emission of the initial excitation pulse, a sequence of electrical pulses is produced by the piezoelectric transducer. The time interval T between two consecutive pulses of this sequence is equivalent to the specimen thickness according to $$T = 2D/V_L$$

where $V_L$ represents the longitudinal ultrasonic wave velocity in the material of the specimen. Other waves such as shear waves can sometimes also be used. For a specific material, the longitudinal ultrasonic wave velocity is usually constant within a wide range of ultrasonic frequencies and the specimen thickness D can be determined by measuring the pulse period T, or its reciprocal.

The time interval between a pulse and its back-reflection or between various reflection pulses can be determined by displaying on an oscilloscope the sinusoidal voltage across the crystal corresponding to the pulse and back-reflections. Thickness of the body being tested can then be read on the horizontal or time axis of the oscilloscope. A more recent development is the direct-reading instrument which displays thickness measurements directly on a meter or on a digital read-out display. In the direct-reading instrument, a constant current source is used to charge a capacitor at a linear rate with respect to time. The constant current source is gated-on by the initial pulse and gated-off by the first back-reflection. The charge on the capacitor is, therefore, dependent on the elapsed time between the initial pulse and the first back-reflection which, in turn, depends on the thickness of the body. The charge on the capacitor at any time is indicated on a meter or a digital-type display. The readout, whether meter or digital-type, is calibrated directly, for example, in inches. Other means are available for measuring this time interval.

U.S. Pat. No. 3,557,610 provides an apparatus for the ultrasonic testing of tubes and other elongated bodies comprising a plurality of ultrasonic transducers, an amplifier for amplifying signals by produced by said transducers when ultrasonic waves fall upon them, sequence control means for permitting passage of signals from said transducers to the amplifier in a cyclic sequence and automatic gain control means for the amplifier incorporating a plurality of pre-settable circuits operable sequentially in synchronism with said sequence control means. Unfortunately, this series of fixed transducers is expensive and does not completely test the circumference of the pipe.

In order to achieve more speed in testing, U.S. Pat. No. 3,415,111 provides a rotary transducer which is capable of moving the transducer elements around the surface of the tubes or rods being tested, while the tube is passed axially thereby. This apparatus comprises a head having therethrough a passage which the test piece is passed axially and a bore parellel to said passage, at least one elongated carrier member received by said bore in the head with its axis parallel to the axis of the passage extending through the head, a crystal transducer element mounted in a recess in said carrier member intermediate to the ends thereof, said crystal transducer element being arranged with the axis normal to its active surface being transverse to the axis of the carrier member, said carrier member being rotatable within the bore for selecting the direction of the normal axis of the crystal transducer element, an ultrasonic pulse generating and receiving instrument, and a pair of coupling means respectively on the carrier member and within said bore in the head electrically coupling the crystal transducer element to said ultrasonic pulse generating and receiving instrument. Unfortunately, the water acting as an accoustical transmitting medium is held within the testing apparatus by seals which protect bearing from water. These seals are subject to wear and can require substantial maintenance. Also, this type of instrument is not made for immersion in an accoustical medium, such as, for example, a water cooling bath in an extrusion line.

U.S. Pat. No. 3,885,419 teaches a method and apparatus for non-desctructive testing of pipes and rods. Several test units in one plane provide right angles to the direction of predominant extension of the object to be tested. Relative rotation is provided between the test units and the pipe or rod to be tested, and on the axis of the latter. The units are alternatingly operated as transmitter and as receiver for ultrasonic pulses, while at least some of the units operate sequentially as transmitter for transmitting ultrasonic pulses in similar directions and into the test object as far as azimuthal component of propagation is concerned. A unit not transmitting in any instant operates as receiver which is particularly angularly displaced from a unit that operates as transmitter in that instant, but will transmit pulses in the same direction when operated as transmitter, then cooperating with another unit displaced further in the same direction and then operating as receiver, etc. This patent does not seem to discuss the problem of dealing with the accoustical medium, that is, containing the medium by seals.

It is an object of this invention to provide a method and apparatus for the rapid ultrasonic detection of flaws and thickness of elongated bodies such as tubes and rods or coatings thereon.

It is an object of this invention to provide a reliable rotary transducer mount for ultrasonic testing which does not contain seals for containing an accoustical medium within.

It is further an object of this invention to provide a rapid ultrasonic detection device for elongated bodies which can be immersed in an acoustical transmitting liquid such as water cooling bath in a polymeric pipe extrusion line.

It is still further an object of this invention to provide an ultasonic testing device which can rapidly test the entire circumference of an elongated body.

SUMMARY OF THE INVENTION

This invention relates to an apparatus for non-destructive ultrasonic testing, such as flaw detection and thickness measurement, of elongated bodies, such as pipes and rods or coatings thereon. Ultrasonic pulses are given off and received back by one or more transducers held in or by a rotating member which can result in testing of the entire circumference of a body. The rotating member is supported by bearings which are resistant to accoustically transmitting liquids such as water, or oil, or others. Generally, the bearings will be functionally disposed so that the bearings support the rotating member within a static member. The resistant nature of the bearings permit the apparatus to operate effectively while substantially submersed, such as totally submersed, in an acoustically transmitting liquid. The rotating member can be rotated on the axis relative to the body being tested around the outer circumference of the body while said body moves axially with respect to said rotating member and while pulses are sent and received by the transducers through the accoustically transmitting liquid to and from the body being tested.

The bearings which support the rotating member are generally of the sleeve or cam-roller type and must be resistant to the accoustically transmitting liquid. This liquid must not have adverse affects on the bearings such as causing wear, swelling, or physical or chemical attack. It is most important that the bearings do not swell when immersed in the transmitting liquid for prolonged periods. For instance, if the liquid is water, materials such as TORLON, Nylon, Teflon, Fibriboid, Rubber, Lignum Vitae, Impregnated Rock Maple, Delrin, Rulon, Graphite and Stellite can be used for the bearings. TORLON, a polyamide-imide material has been found to be quite suitable. Further information dealing with bearing type and composition can be found in MACHINE DESIGN BEARINGS; June 30, 1974; Volume 46; Reference Issue.

The rotating member, generally circular or cylindrical in shape, contains one or more transducers. The larger the number of transducers, the faster a given length of pipe or rod can be tested or the more thorough the testing. Generally, 1–4 transducers are suitable for most testing purposes. When more than one transducer is used, they generally are angularly spaced apart from one another. In a cylinderical rotating member, transducers can be placed on the inside surface or in recesses or in holes therein, or carried within the thickness of the rotating member.

The transducer or transducers are preferably cylindrical focus transducers, that is, those which have a focal point which is roughly a line.

The rotating member is generally supported by bearings within a ystatic member. For example, a cylindrical rotating member can fit within a concentric cylindrical static member. Electrical signals are transferred from the rotating member to the static member for signal interpretation or transfer to other equipment. Signals can be transferred between rotating and static members by slip rings, capacitive coupling or inductive coupling. It is preferred to use inductive coupling, for example, by using coaxial coils located on cylindrical rotating and static members. Wire wound coils are located on the inside of the static member and on the outside of the rotating member. The size of the wire and the number of turns in the coils can be varied to match the electrical properties of the system. This rotary transformer can be found to act as a radio frequency antenna. Typical environments where a rotary mount would be used would have SCR motor control relays in operation which can interfere with the electronic operation of the system. It is often necessary to provide an RF ground and shield.

The rotating member rotates on the axis relative to the elongated body being tested while said body moves axially with respect to said rotating member. It is more convenient to move the body axially while the rotating member rotates in a fixed axial position. Movement of the elongated body is provided by well known means. Rotational motion can be imparted upon the rotating member by well known means, such as an electric motor connected to said member, a drive belt or gears. A toothed drive belt is preferred to prevent slippage while being immersed in an accoustically transmitting liquid. The rotating member is driven at about 0–1000 revolutions per minute, preferably about 0–300 revolutions per minute.

One particularly important application for the invention described herein, is for testing of extruded polymeric pipe. Pipes made of polyethylene, polypropylene, polyvinyl chloride, polystyrene and the like, are often extruded and positioned into a cooling bath, generally of water, to harden. An apparatus such as the one described herein, capable of measuring pipe thickness or detecting flaws and also capable of operating in the water cooling bath is extremely desirable. The water in the bath provides the accoustically transmitting medium which couples the transducer to the pipe. The testing apparatus provides almost instantaneous feedback so that modifications can be made in the pipe extrusion process to compensate for excursions in product quality.

THE DRAWINGS

Referring to the accompanying drawings:

FIG. 3 is a section taken on line 3—3 of FIG. 2.

Figure 1:
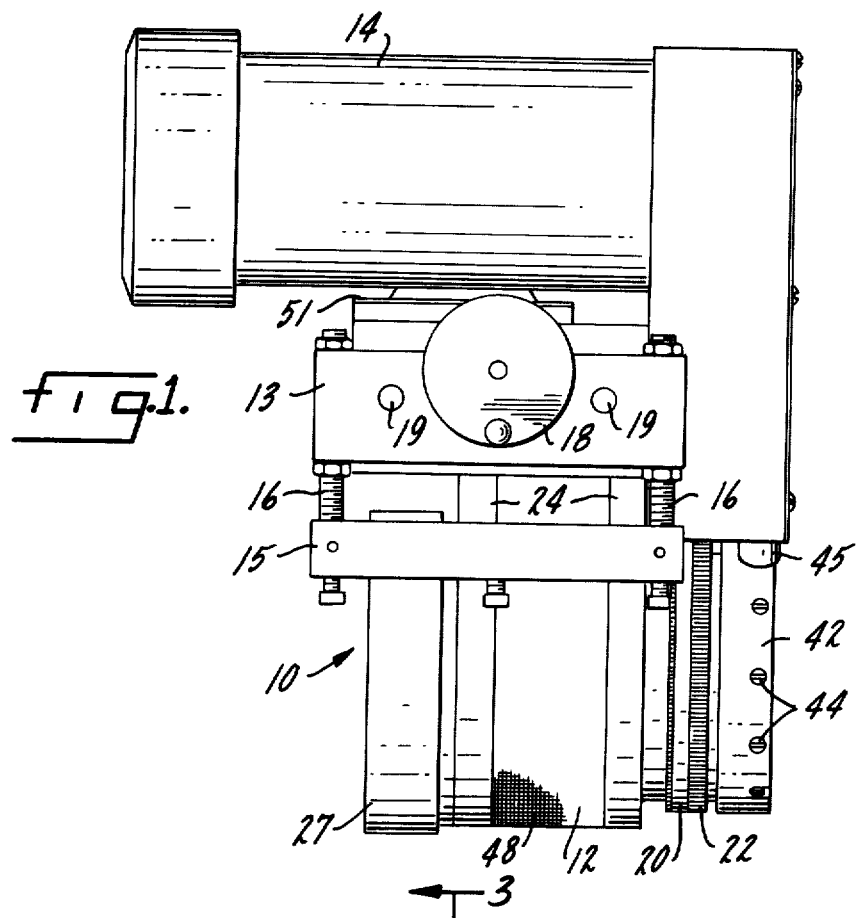
FIG. 1 is a side view of the device.
Figure 2:
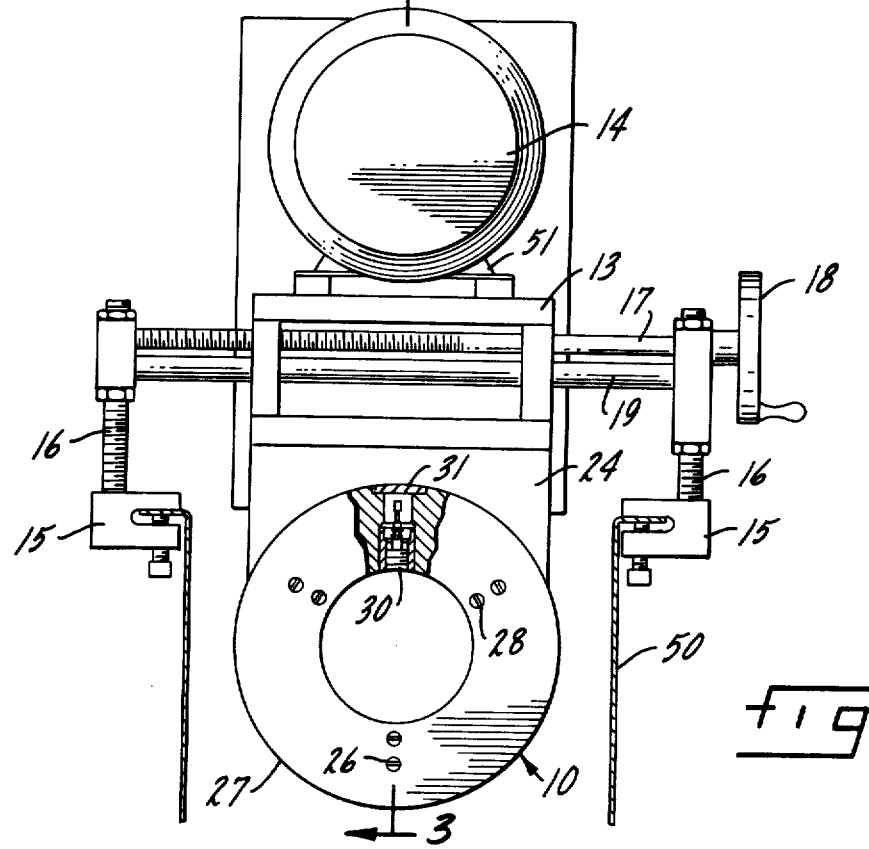
FIG. 2 is a front view looking along the axis of the elongated body to be inspected.

Referring to the figures, the apparatus includes a head assembly 10 having a rotating member 11 and a stationary member 12. The head assembly 10 is supported by a mounting plate assembly 13 with the driving motor 14 resting on the motor mounting plate 51 and the mounting plate assembly 13. The driving motor belt is provided with a sheet metal guard. We have found a Reliance electric ⅓ HP DC motor, Type TR, 1725 RPM to be suitable. A motor-speed controller may also be used to control motor speed and rotational speed of the rotating member. The entire apparatus is attached to, for example, a cooling tank 50 in a pipe extrusion line by the tank clamps 15. Positioning of the apparatus in a cooling tank can be effected by vertical adjustment screws 16 and horizontal adjustment screw 17 with its attached handle 18. When being used to test extruded polymeric pipe, the apparatus is preferably positioned so that the pipe temperature is not rapidly changing. Perpendicularity of the horizontal adjustment motion is maintained by the horizontal guideways 19. Rotational motion is applied to the rotating member 11 via a toothed drive belt 20 driven by an upper drive gear 21 affixed to the shaft of the driving motor 14 and a lower drive gear 22 attached to the rotating member 11 with bolts (not shown). The drive belt should preferably be resistant to the acoustical medium. When the medium is water, a rubber drive belt is adequate. The rotating member 11 is supported by journal bearings 23 affixed in the vertical support plates 24 and acting on bearing races 25. The journal bearings 23 are TORLON$_{tm}$, or other similar material with self-lubricating properties capable of prolonged operation while immersed in water or other fluids as, for example, would be used in pipe production cooling tank operations. The bearing races 25 are constructed of chrome stainless steel or other material compatible with the journal bearing material and the acoustical transmission medium. The bearing races 25 are attached to the rotating member 11 via screws 26.

Referring to FIG. 3., the transducer head assembly 27 is attached via bolts 28 to the rotating member 11. A bore hole 29 is fashioned in the transducer head assembly 27 in which the transducer 30 is placed. Transducer 30 is a cylindrical focus transducer with its line-of-focus perpendicular to the longitudinal axis of the elongated body being tested. It has been found that a 2 inch focal length, ½ inch aperture, 10 megahertz cylindrical focus transducer, such as Sonics, Type IB 10-2, is suitable. During operation, a cover plate 31 which may be water tight is placed over the bore hole 29 via screws (not shown) to reduce turbulence. Any adjustment of the distance from the transducer to the measured pipe is accomplished by loosening the transducer set screw 36 and sliding the transducer 30 in the bore hole 29. The electrical signal is transferred from the transducer 30 via an electrical signal connector 37, such as a Microdot Golden Crimp connector and electrical signal cable 34, such as an RG 174/U. The cable 34 is contained in a machined channel in the rotating member 11. This channel may also contain additional electrical components as may be required for proper damping of the transducer 30.

Signal transfer between the rotating member 11 and the stationary member 12 is effected by a rotary coil or wire 35 and a stationary coil of wire 40. The rotary coil 35 is a number of turns of wire wrapped around the outer circumference of the rotating member 11 and connected to the cable 34. About 7 turns of 18 gauge wire has been found suitable. The stationary coil 40 is a similar coil affixed to the inner circumference of the stationary member 12 and positioned concentrically with the rotary coil 35. The coils 35 and 40 are affixed to their respective members via cement or by imbedding in the head assembly material. The signal from the stationary coil 40 is transferred to the associated external electronics via a signal connector 41.

The angular location of the transducer 30 is determined by means of an indexing head assembly 42. The indexing head assembly 42 is affixed to the rotating member 11 by bolts 43 and contains a number of indexing screws 44 spaced equidistant around its outer circumference. The angular location of these indexing screws 44 are accurately fixed relative to the angular location of the transducer 30 in the transducer head assembly 27. During operation, the proximity of the rotating indexing screws 44 is sensed by the stationary magnetic pickup 45.

A helical slot 46, for example of 1½ turns, may be machined on the inner surface of the rotating member to aid in the movement of fluid around the measured pipe during operation. This movement of fluid can reduce the probability of air bubbles attaching onto or near the transducer, as well as enhancing the cooling of the pipe.

Pressure relief holes 47 are drilled through the stationary member 12 to relieve any excess fluid pressure which could arise in the clearance space between the rotating member 11 and the stationary member 12 while rotating at high speeds.

A copper screen 48 surrounds the outer circumference of the stationary member 12 to reduce electrical interference from external source. Initial alignment of the apparatus can be effected by locating the longitudinal axis of the rotating member 11 approximately coincident with the longitudinal axis of a pipe or elongated body which may be moving axially.

Measurement of the pipe, elongated body or coatings thereon, is effected by ultrasonic pulses which are transferred from transducer 30 to the body and echoes from the body to the transducer 30 via the fluid in which the body, rotating member 11, and stationary member 12 are immersed. The pulses are given off and received back by the transducer 30 while the rotating member 11 is being rotated about the body to be tested by motor 14 and drive belt 20.

We claim:

1. An apparatus for the ultrasonic non-destructive testing of elongated bodies or coatings thereon comprising a rotating member holding one or more cylindrical focus transducers, said transducers capable of sending ultrasonic pulses and receiving corresponding echo pulses back as said rotating member is rotated on the axis relative to the body being tested while said body moves axially with respect to said rotating member, said apparatus containing water resistant bearings, functionally disposed for supporting the rotating member.

2. The apparatus of claim 1 wherein the bearing is made of TORLON.

3. The apparatus of claim 1 wherein the rotating member contains from 1 to 4 cylindrical focus transducers.

4. An apparatus for the non-destructive ultrasonic testing of elongated bodies comprising:
- a rotating member holding one or more cylindrical focus transducers and capable of rotation about the axis of an elongated body;
- a static member; and
- bearings functionally disposed so that said bearings support the rotating member within the static member and said bearing being resistant to an acoustically transmitting liquid.

5. The apparatus of claim 4 wherein the bearings are TORLON.

6. The apparatus of claim 4 wherein the rotating member contains from 1 to 4 cylindrical focus transducers.

7. The apparatus of claim 4 wherein the rotating member and static member are concentric cylinders.

8. The apparatus of claim 7 wherein the rotating member and static member each has a coaxial coil which couple with one another inductively.

9. The apparatus of claim 4 wherein the rotating member is driven by an electric motor.

10. The apparatus of claim 9 wherein the rotating member can be rotated at about 0–1000 revolutions per minute.

11. The apparatus of claim 10 wherein the rotating member can be rotated at about 0–300 revolutions per minute.

12. An apparatus for the non-destructive ultrasonic testing of elongated bodies which comprises a rotor member holding one or more cylindrical focus transducers, and a static member which supports said rotor member by means of bearings, said apparatus being substantially immersed in an acoustically transmitting liquid, and said bearings being resistant to physical or chemical attack by said liquid.

13. The apparatus of claim 12 wherein the bearings are resistant to water.

14. The apparatus of claim 13 wherein the bearings are TORLON.

15. A method for the ultrasonic non-destructive testing of elongated bodies or coatings thereon comprising rotating an apparatus holding one or more cylindrical focus transducers while said transducers send ultrasonic pulses and receive corresponding echo pulses back as said apparatus is rotated on the axis relative to the body being tested while said body moves axially with respect to said apparatus and while said apparatus is substantially submersed in an acoustically transmitting liquid.

16. The method of claim 15 wherein the apparatus contains water resistant bearings.

17. The method of claim 15 wherein the apparatus contains from 1 to 4 cylindrical focus transducers.

18. An apparatus for the ultrasonic non-destructive testing of elongated bodies or coatings thereon comprising a rotating member holding one or more transducers, said transducers capable of sending ultrasonic pulses and receiving corresponding echo pulses back as said rotating member is rotated on the axis relative to the body being tested while said body moves axially with respect to said rotating member, said apparatus containing Torlon bearings, functionally disposed for supporting the rotating member.

19. An apparatus for the non-destructive ultrasonic testing of elongated bodies comprising:
- a rotating member holding one or more transducers and capable of rotation about the axis of an elongated body;
- a static member; and
- Torlon bearings functionally disposed so that said bearings support the rotating member within the static member and said bearings being resistant to an acoustically transmitting liquid.

20. An apparatus for the non-destructive ultrasonic testing of elongated bodies which comprises a rotor member holding a transducer or transducers, and a static member which supports said rotor member by means of Torlon bearings, said apparatus being substantially immersed in an acoustically transmitting liquid, and said bearings being resistant to physical or chemical attack by said liquid.

* * * * *